United States Patent [19]

Hollingsbee

[11] 4,347,238

[45] Aug. 31, 1982

[54] AUTOCLAVABLE EMULSION CONTAINING SILVER SULPHADIAZINE

[75] Inventor: Derek A. Hollingsbee, Chelmsford, England

[73] Assignee: Smith & Nephew Associated Companies Limited, England

[21] Appl. No.: 200,429

[22] Filed: Oct. 24, 1980

[30] Foreign Application Priority Data

Oct. 26, 1979 [GB] United Kingdom ............... 7937183

[51] Int. Cl.$^3$ ..................... A61K 31/78; A61K 31/00; A61K 47/00; A61K 31/555

[52] U.S. Cl. ...................................... 424/81; 424/170; 424/245

[58] Field of Search .................... 424/81, 78, 245, 170

[56] References Cited

U.S. PATENT DOCUMENTS

| | | | |
|---|---|---|---|
| 3,608,073 | 9/1971 | Phares, Jr. et al. | 424/168 |
| 3,639,577 | 2/1972 | Urton et al. | 424/88 |
| 3,790,665 | 2/1974 | Gilds et al. | 424/81 |
| 3,920,810 | 11/1975 | Rankin | 424/81 |
| 4,083,974 | 4/1978 | Turi | 424/81 |
| 4,177,056 | 12/1979 | Mueller et al. | 424/81 |
| 4,200,561 | 4/1980 | Chang | 424/81 |
| 4,250,163 | 2/1981 | Nagai et al. | 424/81 |

FOREIGN PATENT DOCUMENTS

| | | |
|---|---|---|
| 2007091 | 5/1979 | United Kingdom . |
| 2008946 | 6/1979 | United Kingdom . |
| 2013084 | 8/1979 | United Kingdom . |

OTHER PUBLICATIONS

The Merck Index-9th Ed.-Item 8693 (1976)-Merck & Co. Index.
Martindale, The Extra Pharmacopoeia, 1977, p. 919.
Chem. Abst. 86, 1977, 115287s.
Chem. Abst. 85, 1976, 25348n.
Chem. Abst. 52, 1958, 20883b.

*Primary Examiner*—Douglas W. Robinson
*Attorney, Agent, or Firm*—Jacobs & Jacobs

[57] ABSTRACT

A mobile, drop-forming heat-sterilizable ophthalmic oil-in-water emulsion which comprises an aqueous solution of a pharmaceutically acceptable salt of polyacrylic acid lightly cross-linked with triallyl sucrose, a pharmaceutically acceptable oil and a medicament effective when applied topically to the eye and sterilizable by autoclaving is described.

6 Claims, No Drawings

AUTOCLAVABLE EMULSION CONTAINING SILVER SULPHADIAZINE

The present invention relates to a heat sterilizable oil-in-water emulsion suitable for application to the eye and to its preparation and use.

It is conventional to administer water-soluble pharmaceutically active compounds such as anti-infective agents and anti-inflammatory agents topically to the eye in the form of an aqueous solution of the compound. However no wholly satisfactory manner has previously been found to administer sparingly soluble or water-insoluble pharmaceutically active compounds topically to the eye. In the past such compounds have been formulated as oily solutions, ointments, suspensions and gels. Oily solutions have difficulty in being accepted into the aqueous environment of the eye and are often expelled to run down the cheek. Ophthalmic ointments which generally contain petroleum jelly or a mixture of petroleum jelly and liquid paraffin as a base also are not hydrophilic and may therefore be dislodged or may not effectively wet the cornea and mucous membrane thereby not releasing an effective amount of the pharmaceutically active compound. Ophthalmic suspensions often suffer from the disadvantage that the pharmaceutically active compound separates out on standing so that the suspension must be reformed before use. Some authorities believe that such prolonged shaking is required to achieve sufficient homogeneity that many patients are administering drops which are under strength.

Some of the disadvantages of ointments and suspensions may be overcome using an aqueous gel as an ophthalmic vehicle. British Patent Specification No. 2007091A discloses a gel comprising an aqueous solution of a carboxyvinyl polymer, a water-soluble basic substance and an ophthalmic drug admixed therewith. These gels are thick and are applied in a similar manner to ointments. They therefore rely on an adequate amount of tears being present for their ultimate dispersal in the eye. Some authorities would prefer to apply an ophthalmic drug in a more mobile form which can spread rapidly.

British Patent Specification No. 2008946A discloses creams which employ inter alia a cross-linked acrylic acid salt as a thickening agent. Such creams were said to be for use on the skin and no ophthalmic use is disclosed. Indeed since the creams contain particularly large amounts of analgesic agent their use in the eye would appear undesirable.

It is now appreciated that an emulsion may advantageously be used for delivering medicaments to the eye. The small difference in specific densities between immiscible liquids such as oil and water leads to a reduced tendency for the components to separate out. In particular, water-insoluble pharmaceutically active compounds may be dissolved or suspended in an oil-in-water emulsion. The sterilization of known oil-in-water emulsions by heat tends to produce coalescence of the dispersed oil phase and attempts to remedy this by excessive agitation may lead to creaming. The addition of conventional emulsion stabilizers such as gelatin, dextran and methylcellulose helps to some extent but the resulting emulsions are still adversely affected by elevated temperature.

It has now been discovered that a polyacrylic acid lightly cross-linked with triallyl sucrose such as a Carbopol (Registered Trade Mark of B. F. Goodrich) can be employed to form an oil-in-water emulsion that is particularly apt for application to the eye and which has the additional considerable advantage of being heat sterilizable, for example by autoclaving. This ability of the emulsion to withstand sterilization by heat without breaking allows for flexibility in manufacture, for example by eliminating the need for aseptic fabrication.

The present invention provides a mobile, drop-forming heat-sterilizable ophthalmic oil-in-water emulsion which comprises an aqueous solution of a pharmaceutically acceptable salt of polyacrylic acid lightly cross-linked with triallyl sucrose, a pharmaceutically acceptable oil and a medicament effective when applied topically to the eye.

A favoured aspect of the invention provides an emulsion of the present invention which has been heat sterilized, for example by autoclaving. Pharmaceutical compositions when presented for topical application to the eye are most suitably in a sterile condition. Conventionally sterilization is carried out using heat, for example by autoclaving. For autoclaving, the emulsion is sealed into a container, for example a single or multidose pack and then subject to conditions of elevated temperature and pressure for sufficient time to ensure sterility of the emulsion. Conventional autoclaving conditions include the following:-15 minutes at 121° C. and 15 psi pressure; or 30 minutes at 116° C. and 10 psi pressure; or 30 minutes at 100°–102° C. and atmospheric pressure provided the emulsion additionally contains a bactericide. Emulsions of the present invention are stable to such autoclaving conditions which is most advantageous.

Suitable polyacrylic acids lightly cross-linked with triallyl sucrose for use in the present invention are the Carbopols (Registered Trade Mark of B. F. Goodrich). Favoured Carbopols are Carbopol 934, Carbopol 940 and Carbopol 941. A preferred Carbopol is Carbopol 941 which provides particularly good stability to the emulsion before and after heat sterilization without affecting the mobility of the emulsion adversely.

The amount of the cross-linked polyacrylic acid present in the invention is normally 0.04 to 0.25% (percentages when referred to herein mean % by weight) of total emulsion, more aptly 0.05 to 0.2% and preferably 0.06 to 0.16%. This quantity of cross-linked polyacrylic acid after neutralisation produces a mobile, drop forming emulsion capable of heat sterilization when present in a conventional oil-in-water emulsion. A dispersion of the cross-linked polyacrylic acid neutralized with a pharmaceutically acceptable base in aqueous solution increases the viscosity of the water.

Suitable pharmaceutically acceptable bases which will form salts with the cross-linked polyacrylic acid include organic nitrogenous bases, for example alkyl amines, dialkyl amines, trialkylamines, alkanolamines, dialkanolamines and trialkanolamines or aqueous solutions of ammonia or alkali metal hydroxides. A preferred base is an aqueous solution of sodium hydroxide. Suitably the amount of sodium salt of cross-linked polyacrylic acid will be between 0.04 and 0.25%, more aptly between 0.05 and 0.2% and preferably between 0.06 and 0.16% of the emulsion.

The neutralization of the cross-linked acrylic acid with the pharmaceutically acceptable base is generally adjusted so that the resultant solution has a pH of 5 to 8 more aptly 6.5 to 7.5 and preferably 7. The final value of the pH may be affected by the stability of the medicament to be incorporated in the emulsion.

Unlike conventional emulsions the viscosity of the emulsion of this invention is not disadvantageously reduced by exposure to elevated temperatures. Thus the emulsions of this invention prepared at ambient temperatures can be sterilized at elevated temperatures without unacceptable damage.

Use of large quantity (for example greater than 0.3%) of the salt of a lightly cross-linked polyacrylic acid tends to gel the water phase making the emulsion immobile and should therefore be avoided.

To provide an emulsion which is suitable for application to the eye to provide a readily dispersed dosage form the viscosity of the emulsion is suitably less than 500 centipoises and more suitably between 35 and 350 centipoises. Emulsions with viscosities between 50 and 150 centipoises have particularly apt properties of dispersibility and stability to sterilization by heat. Viscosities may be measured using a Ferranti-Shirley Cone and plate Viscometer using a 7 cm diameter cone at a shear rate of 172 cm$^{-1}$ at a temperature of 20° C. on a sample size of 1 to 2 ml.

Normally any pharmacologically acceptable oil may be used in the emulsions of the present invention. Suitably these oils include vegetable or mineral oils such as castor oil, liquid paraffin, olive oil, almond oil, arachis oil, squalene and silicones. Suitably the amount of oil present will be between 1 and 45% by weight of the emulsion and will preferably be between 5 and 40% of the emulsion. Favoured oils for use in this invention include castor oil and liquid paraffin.

The amount of oil and type of oil will vary depending on the solubility or otherwise of the medicament in the oil. For example a finely divided solid medicament will generally require a smaller volume of oil (such as 5% to 15%) to merely suspend the particles than would be needed to dissolve an oil soluble medicament (such as 15% to 40%).

Normally the emulsions of the present invention will include one or more surfactants or emulsifying agents. Particularly apt surfactants are non-ionic surfactants. Suitable non-ionic surfactants include sorbitan fatty acid esters (Arlacels, Registered Trade Mark of Honeywill-Atlas Ltd.) polyoxyethylated sorbitan fatty acid esters (Tweens, Registered Trade Mark of Honeywill-Atlas Ltd) and polyoxyethylated-polyoxypropylene diol block copolymers (Pluronics, Registered Trade Mark of BASF Wyandotte Corp.). An emulsifier comprising a mixture of an Arlacel and a Tween has been found to possess the correct balance of hydrophilic and lipophilic properties to provide a stable emulsion at ambient temperatures. A preferred emulsifier comprises a mixture of sorbitan mono-oleate (Arlacel 80 and polyoxyethylated sorbitan mono-oleate (Tween 80) most aptly in a ratio of between 1:2 and 2:1. Suitably the amount of emulsifier in the emulsion present is from 0.5 to 2.5% and preferably from 0.75 to 1.5% of the emulsion. Generally the higher the amount of oil present the higher the amount of emulsifier will be required.

Preferably the medicament will be within the oil phase which is dispersed in the composition. It has been found that this prevents undue separation of active agent from the emulsion.

In one particularly apt form of this invention the medicament will be present as a finely divided solid. The particle size of the solid will be small enough to be impalpable. A favoured solid medicament for the present invention is silver sulphadiazine which is an effective antibacterial. In a preferred form the silver sulphadiazine is in its micronized form. In this state of subdivision the material is such that 99% of the particles are less than 20 microns in diameter and 90% less than 10 microns. In practice the majority of the particles have a diameter in the range 1 to 5 microns. Suitably the amount of silver sulphadiazine present is between 0.05 and 2.0% and aptly 0.1 to 1.6%. A favoured amount of silver sulphadiazine to be used will be 0.6 to 1.4% and will preferably be 1%.

In a preferred form the present invention provides a mobile, drop-forming, heat sterilizable ophthalmic oil-in-water emulsion which comprises an aqueous solution containing 0.06 to 0.16% of a pharmaceutically acceptable salt of a cross-linked polyacrylic acid lightly cross-linked with triallyl sucrose, 5 to 15% of a pharmacologically acceptable oil, 0.6 to 1.4% of finely divided silver sulphadiazine and 0.75 to 1.5% of emulsifier.

A particularly apt oil for use in this aspect of the invention is liquid paraffin. The oil for use in this aspect of the invention is most suitably present from 6 to 10%. Most aptly the sodium salt of the cross-linked polyacrylic acid is employed and is favourably present at 0.1%. In this aspect of the invention the silver sulphadiazine is preferably present in micronized form at 1%. The emulsifier is most aptly present by 0.9 to 1.1%, for example 1% and aptly comprises a mixture of polyethoxylated sorbitan mono-oleate and sorbitan mono-oleate.

A particularly preferred emulsion of the present invention comprises a mobile drop-forming heat sterilizable ophthalmic emulsion which comprises an aqueous solution containing 0.1% of a sodium salt of a polyacrylic acid lightly cross-linked with triallyl sucrose, 6 to 10% liquid paraffin, 1% micronized silver sulphadiazine and 1% of a mixture of polyethoxylated sorbitan mono-oleate and sorbitan mono-oleate. Most aptly this emulsion contains 8% liquid paraffin. Most aptly this emulsion contains 0.57% of polyethoxylated sorbitan mono-oleate and 0.43% of sorbitan mono-oleate.

In this aspect of the invention the silver sulphadiazine may be in the oil, in the water or in both. Generally it is preferred that the silver sulphadiazine is predominantly in the water, for ease of manufacturing such a product.

The present invention also envisages the topical treatment of bacterial and fungal infections of the eye with a heat sterilized emulsion of the invention containing silver sulphadiazine. Among the serious bacterial infections of the eye is postoperative bacterial endophthalmitis which is often caused by *Staphylococci* or gram negative organisms including *Pseudomonas aeruginosa, Escherichia coli,* and *Proteus mirabilis.* Heat sterilizable emulsions of the present invention containing silver sulphadiazine in a unit dose or multi-dose pack are suitable for treatment of such infections. The preferred presentation is in a multidose pack form comprising a polyethylene container of volume 5 to 15 ml fitted with a dropper capable of delivering a drop of between 20 to 50μ liters. for example 30μ liters. The preferred dose comprises 1 to 4 drops (that is 20 to 200μ liters) containing from 0.2 to 5.0 mg for example 0.3 to 1.4 mg of silver sulphadiazine four times a day. The heat sterilized emulsion containing silver sulphadiazine may also be used prophylactically to prevent post-operative infection and against the infections of the conjunctiva, eyelids and cornea caused by organisms such as *Staphylococci* and the *Streptococci.*

In another apt form of this invention the medicament will be dissolved in the oil. Suitable medicaments include anti-inflammatory steroids which are oil soluble and effectively water insoluble. Particularly preferred anti-inflammatory steroids include cortisone, hydrocortisone, fludrocortisone, dexamethasone, fluormethalone, prednisolone, triamcinaolone, betamethasone, flumethasone, fluocinolone, methylprednisolone, trimeloxone, medrysone, hydrocortisone acetate, betamethasone valerate, betamethasone proprionate, betamethasone benzoate, fluocinolone acetate, triamcinolone acetonide and prednisolone acetate.

Suitably the anti-inflammatory steroids will be present in an amount from 0.05 to 2% and more preferably from 0.1 to 1.)%.

In a preferred form the present invention provides a mobile drop-forming heat sterilizable ophthalmic oil-in water emulsion which comprises an aqueous solution containing 0.06 to 0.16% of a pharmaceutically acceptable salt of a polyacrylic acid lightly cross-linked with triallyl sucrose, 15 to 40% of a pharmacologically acceptable oil, 0.05 to 2% of an anti-inflammatory steroid and 0.05 to 2.5% of emulsifier.

A favored oil for use in aspects of the invention containing an anti-inflammatory steroid is castor oil. A favored emulsifier for use in such forms of the invention is a mixture of sorbitan mono-oleate and polyethoxylated sorbitan mono-oleate. An emulsifier which is favored for use in such forms of the invention is a mixture of polyoxyethylene and polyoxypropylene diol block copolymers.

In a particularly preferred form the present invention provides a mobile, drop-forming heat sterilizable ophthalmic oil-in-water emulsion which comprises an aqueous solution containing 0.6 to 0.16% of the sodium salt of a polyacrylic acid lightly cross-linked with triallyl sucrose, 15 to 40% of a pharmaceutically acceptable oil, 0.1 to 1% of an anti-inflammatory steroid and 1 to 2% of emulsifier.

In a further apt form of the present invention the emulsion containing an anti-inflammatory steroid will also contain an antibacterial agent. The antibacterial agent may be present as a finely divided solid in the oil phase or a solution in the oil or a solution in the aqueous phase. If the antibacterial agent is present in the aqueous phase it must be compatible with the cross-linked polyacrylic acid. The amount of antibacterial agent present is suitably between 0.1 and 2%, more preferably 0.25 and 1% of the emulsion. Suitable antibacterial agents for the invention include chloramphenicol and sulphacetamide sodium. A preferred antibacterial is chloramphenicol.

In a particularly preferred form the present invention provides a mobile, drop-forming, heat sterilizable ophthalmic oil-in-water emulsion which comprises an aqueous solution containing 0.06 to 0.16% of a pharmaceutically acceptable salt of a cross-linked polyacrylic acid lightly cross-linked with triallyl sucrose, 15 to 40% of a pharmacologically acceptable oil, 0.1 to 1.0% of an anti-inflammatory steroid, 0.25 to 1% of an antibacterial agent and 1.0 to 2.0% of emulsifier.

Accordingly a further aspect of the invention extends to the topical administration of heat sterilized emulsion of the present invention containing an anti-inflammatory steroid or an anti-inflammatory steroid and an antibacterial agent for the treatment of various inflammatory diseases of the eye such as keratitis, indocyclitis, scleritis, blepharitis or bacterial conjuctivitis.

The sterile emulsions of the present invention containing an anti-inflammatory steroid or an anti-inflammatory steroid/antibacterial combination are suitably provided as unit dose or multidose packs. Preferred is a multidose pack comprising the heat sterilized emulsion in a polyethylene or glass bottle fitted with a dropper capable of delivering a drop of 50μ liters. The dose and frequency will vary depending upon the type of inflammation encountered, for example for post operative inflammation after cateract removal, the initial treatment may be as frequent as 1 to 2 drops every 1 to 2 hours which, when a response is noted, is reduced to 1 to 2 drops 3 times a day; for chronic conjunctivitis or blepharitis the dose may be 1 to 2 drops 4 times a day.

A further aspect of the invention provides the emulsion of the present invention in a unit dose pack presentation comprising a package capable of withstanding heat sterilization containing a suitable amount of the emulsion. Suitable packages are described in British Pat. No. 1,275,903. Suitably the single dose presentation provides 0.2 to 0.5 ml. of heat sterilized emulsion.

Another aspect of the invention provides the emulsion of the present invention in a multidose pack presentation comprising a package capable of withstanding heat sterilization containing a suitable amount of the emulsion. Suitable packages include glass bottles in clear or amber glass provided with a dropper or a plastics bottle with an integral drop delivering outlet. Normally the emulsion of a multidose pack presentation will contain an ophthalmically acceptable preservative. The preservative if present in the aqueous phase must be compatible with the cross-linked polyacrylic acid. Suitable preservatives include chlorbutanol, thimerosal and phenylethanol. A preferred preservative system is thimerosol and phenylethanol. The preservative will generally be present in an amount from 0.001 to 0.5% of the emulsion. A preferred preservative system comprises 0.01% thimerosol and 0.5% phenylethanol.

The emulsions of the present invention may be prepared by heating together at elevated temperature the pharmacologically acceptable oil, the emulsifying agents and the medicament with stirring until the medicament has dissolved or dispersed in the oil. A suitable elevated temperature lies between 55° and 75° C., for example 60° C. The cross-linked polyacrylic acid is dispersed in water and neutralized, that is the pH of the solution is adjusted to 5 to 8, more suitably to 6.5 to 7.5 and preferably to 7 by addition of a solution of a pharmaceutically acceptable base, for example sodium hydroxide solution. This solution may also be heated to an elevated temperature, for example 60° C. The aqueous solution is added to the oil phase with vigorous mixing. The emulsion formed is allowed to cool and then the final weight adjusted with water. The emulsion may then be filled into the appropriate pack.

Alternatively if the medicament is present as a finely divided solid, a portion of the aqueous solution is taken and the solid dispersed in it. This dispersion is then added into the emulsion formed from the rest of the aqueous solution and the oil at an elevated temperature with vigorous stirring. The emulsion is then allowed to cool with stirring. Dispersing the solid in a portion of the aqueous phase provides an even dispersion of the solid into the oil phase avoiding the clumping which may take place if the solid is added directly to the emulsion.

The emulsion when cool is filled and sealed into a unit dose or multi-dose container in conventional manner. The sealed containers are conveniently sterilized by autoclaving, for example at 116° C. at 10 psi for 30 minutes. After autoclaving the emulsions are sterile and present in their packs ready for use for topical application to the eye.

EXAMPLE 1

An antimicrobial oil-in-water emulsion containing silver sulphadiazine in the oil phase was prepared from the following:
Silver sulphadiazine: 1.0%
Liquid paraffin: 8.0%
Polyoxyethylated sorbitan mono-oleate: 0.57%
Sorbitan mono-oleate: 0.43%
Cross-linked polyacrylic acid: 0.1%
Water to 100%

The emulsion was stable to autoclaving. (The polyoxyethylated sorbitan monooleate was Tween 80; the sorbitan mono-oleate was Arlacel 80 and the cross-linked polyacrylic acid was Carbopol 941).

The cross-linked polyacrylic acid was dispersed in water and the pH adjusted to a value of 7 with sodium hydroxide solution. Part of this solution (80 ml) was heated to 65°–70° and added with stirring to the liquid paraffin, Tween 80 and Arlacel 80 which had previously been mixed together and heated to a similar temperature.

The silver sulphadiazine was dispersed in the remaining cross-linked polyacrylic acid solution and added to the emulsion with stirring. The emulsion was allowed to cool with continued stirring and made up to the correct weight with water.

The emulsion was sealed into suitable single dose or multi-dose eye dropper bottles. The emulsion was stable to sterilization by autoclaving at 116° C. for 20 minutes.

The viscosity of the emulsion was measured before and after autoclaving at 116° C. for 30 minutes using a Ferranti-Shirley Cone and Plate Viscometer using a 7 cm diameter cone at a shear rate of 172 cm$^{-1}$ at a temperature of 20° C. and gave a value of 138 centipoise before autoclaving and 124 centipoise after autoclaving.

Demonstration of Effectiveness

(a) Microbiology

The efficacy of the emulsion of the present invention containing 1% silver sulphadiazine as a bactericidal agent was shown by a zone diffusion test. A small cell 8 mm in diameter was cut in the center of an agar plate seeded with the appropriate test organism. This cell was filled with the emulsion and the plates incubated. The resultant zone of inhibited growth of the organism around the cell was then measured, the results obtained were:

| Organism | Mean Zone Diameter (mm) (including 8mm cell) |
| --- | --- |
| *Staphylococcus aureus* | 37.5 |
| *Pseudonomas aeruginosa* | 24.7 |
| *Proteus mirabilis* | 16.5 |

(b) Stability to Autoclaving and Storage

The silver sulphadiazine content of an emulsion was measured before and after autoclaving at 115° C. for 30 minutes by high-pressure liquid chromatography with the following results:

| | % Silver sulphadiazine |
| --- | --- |
| Before autoclaving | 0.981 |
| After autoclaving | 0.988 |

Autoclaved emulsions containing 1% silver sulphadiazine were aged at 5°, 20°, 40° and 50° C. for 3 months without loss of silver sulphadiazine content or any breakdown of the emulsion.

(c) Acceptability

Emulsions containing 1% silver sulphadiazine were autoclaved at 116° C. for 30 minutes and a drop study carried out on human volunteers. A drop of the autoclaved emulsion was installed into one eye of thirty human volunteers without any adverse reactions noted.

EXAMPLE 2

An anti-inflammatory oil-in-water emulsion containing hydrocortisone was prepared from the following:
Hydrocortisone: 0.5%
Castor Oil: 40%
Pluronic L 122: 1.5%
Pluronic L 103: 0.5%
Cross-linked polyacrylic acid: 0.1%
Sodium hydroxide to neutralise the polyacrylic acid dispersion to pH 7.
Distilled water to 100%.

(Pluronic L 122 is a liquid polyoxyethylene-polyoxypropylene diol block copolymer of MW 5000, containing 20% poly(oxyethylene) units; Pluronic L 103 is a polyoxyethylene-polyoxypropylene diol block copolymer of MW 4650 containing 30% poly(oxyethylene) units).

The cross-linked polyacrylic acid was dispersed in the water and the pH of the solution adjusted to pH 7 with sodium hydroxide solution. The hydrocortisone was dissolved in the castor oil and Pluronics and heated to 60° C. The oily solution was then added to the cross-linked polyacrylic acid solution which had similarly been heated to 60° C. The mixed solutions were allowed to cool while stirring. The emulsion formed was stable to sterilization by autoclaving.

EXAMPLE 3

An anti-inflammatory oil-in-water emulsion containing dexamethasone was prepared from the following:
Dexamethasone: 0.1%
Castor Oil: 20%
Polyoxyethylated sorbitan mono-oleate: 0.33%
Sorbitan mono-oleate: 0.66%
Cross-linked polyacrylic acid: 0.15%
Sodium hydroxide to neutralize Carbopol dispersion to pH 7.
Distilled water to 100%

(The polyoxyethylated sorbitan mono-oleate was Tween 80; the sorbitan mono-oleate was Arlacel 80 and the cross-linked polyacrylic acid was Carbopol 941).

The oil-in-water emulsion was made up as described in Example 4.

EXAMPLE 4

An anti-inflammatory and antibacterial oil-in-water emulsion containing dexamethasone and chloramphenicol was prepared from the following:
Dexamethasone: 0.1%
Chloramphenicol: 0.5%

Castor oil: 20.0%
Polyoxyethylated sorbitan mono-oleate: 0.33%
Sorbitan mono-oleate: 0.66%
Cross-linked polyacrylic acid: 0.15%
Sodium hydroxide solution to neutralize the Carbopol dispersion to pH 7.
Distilled water to 100%

(The polyoxyethylated sorbitan mono-oleate was Tween 80; the sorbitan mono-oleate was Arlacel 80 and the cross-linked polyacrylic acid was Carbopol 941).

The dexamethasone and chloramphenicol were dissolved in the castor oil. The Tween 80 and the Arlacel 80 were added and the oily solution heated to 65° C. while being stirred. The Carbopol 941 was dispersed in the water and neutralized with aqueous sodium hydroxide to give the solution a pH value of 7. This solution was heated to 65° C. and added with brisk stirring to the oily solution containing medicaments and emulsifiers. The resulting emulsion was allowed to cool while being stirred. The emulsion was stable to heat sterilization by autoclaving at 116° C. for 30 minutes. The emulsion had a viscosity of 132 centipoise before autoclaving and 66 centipoise after autoclaving when measured on the viscometer of Example 1 at 25° C.

EXAMPLE 5

An antimicrobial oil-in-water emulsion containing silver sulphadiazine in the oil phase was prepared from the following:

Silver sulphadiazine: 1.0%
Liquid Paraffin: 8.0%
Polyethoxylated sorbitan mono-oleate: 0.51%
Sorbitan mono-oleate: 0.43%
Cross-linked polyacrylic acid: 0.1%
Water to 100%

(The polyoxyethylated sorbitan mono-oleate was Tween 80; the sorbitan mono-oleate was Arlacel 80 and the cross-linked polyacrylic acid was Carbopol 941).

A suspension of the Carbopol in the water was prepared and neutralized with sodium hydroxide solution. The silver sulphadiazine, Tween and Arlacel were dissolved or dispersed in the liquid paraffin and heated to 60° C. prior to addition of the Carbopol suspension with vigorous mixing. The emulsion formed was stirred until cool and made up to weight with water.

The emulsion was stable to autoclaving.

What we claim is:

1. A heat sterilized, mobile, drop-forming, ophthalmic oil-in-water emulsion which comprises an aqueous solution of 0.04 to 0.25% of a pharmaceutically acceptable salt of polyacrylic acid lightly cross-linked with triallyl sucrose, a pharmacologically acceptable vegetable or mineral oil and a therapeutically effective amount of finely divided silver sulphadiazine.

2. An emulsion as claimed in claim 1 which has been sterilized by autoclaving.

3. An emulsion as claimed in claim 2 which comprises 0.05 to 0.2 wt.% of polyacrylic acid lightly cross-linked with triallyl sucrose.

4. An emulsion as claimed in claim 3 in which the viscosity of the emulsion is in the range of 50 to 150 cps.

5. A heat sterilized, mobile, drop-forming, ophthalmic oil-in-water emulsion which comprises an aqueous solution containing 0.06 to 0.16% of a pharmaceutically acceptable salt of a cross-linked polyacrylic acid lightly cross-linked with triallyl sucrose, 5 to 15% of a pharmacologically acceptable vegetable or mineral oil, 0.6 to 1.4% of finely divided silver sulphadiazine and 0.75 to 1.5% of emulsifier selected from the group consisting of sorbitan fatty acid esters, polyoxyethylated sorbitan fatty acid esters and polyoxyethylated-polyoxypropylene diol block copolymers.

6. A heat sterilized, mobile, drop forming, ophthalmic oil-in-water emulsion consisting essentially of an aqueous solution containing 0.06 to 0.16% of a pharmaceutically acceptable salt of a cross-linked polyacrylic acid lightly cross-linked with triallyl sucrose, 5 to 15% of a pharmacologically acceptable vegetable or mineral oil, a therapeutically effective amount of finely divided silver sulphadiazine effective when applied topically to the eye, and 0.75 to 1.5% of an emulsifier selected from the group consisting of sorbitan fatty acid, esters, polyethoxylated sorbitan fatty acid esters and polyethylated-polyoxypropylene diol block copolymers.

* * * * *